United States Patent
Maiti et al.

(10) Patent No.: US 11,313,860 B2
(45) Date of Patent: Apr. 26, 2022

(54) SCREENING KIT FOR DETECTION OF GRADES OF CERVICAL CANCER AND PROCESS FOR THE PREPARATION THEREOF

(71) Applicant: Council of Scientific & Industrial Research, New Delhi (IN)

(72) Inventors: Kaustabh Kumar Maiti, Thiruvnanthapuram (IN); Varsha Karunakaran, Thiruvananthapuram (IN); Kunjuraman Sujathan, Thiruvananthapuram (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 17/046,183

(22) PCT Filed: Jul. 24, 2019

(86) PCT No.: PCT/IN2019/050540
§ 371 (c)(1),
(2) Date: Oct. 8, 2020

(87) PCT Pub. No.: WO2020/021568
PCT Pub. Date: Jan. 30, 2020

(65) Prior Publication Data
US 2022/0065860 A1    Mar. 3, 2022

(30) Foreign Application Priority Data

Jul. 26, 2018    (IN) .............................. 201811028087

(51) Int. Cl.
*G01N 33/574*    (2006.01)
*G01N 21/65*    (2006.01)
(Continued)

(52) U.S. Cl.
CPC ...... *G01N 33/57411* (2013.01); *G01N 1/2813* (2013.01); *G01N 1/4077* (2013.01);
(Continued)

(58) Field of Classification Search
CPC ...................... G01N 33/57411; G01N 21/658
See application file for complete search history.

(56) References Cited

U.S. PATENT DOCUMENTS 8,716,443 B2 *  5/2014  Druilhe ................ A61K 39/015
                                                        530/350
8,748,578 B2    6/2014  Bamberg et al.
(Continued)

FOREIGN PATENT DOCUMENTS

| CN | 1582341 A | * | 2/2005 | .......... C12Q 1/6881 |
|---|---|---|---|---|
| CN | 106137970 A | | 11/2016 | |
| JP | 2013/544494 A | | 12/2013 | |

OTHER PUBLICATIONS

Jennifer Connolly, "Non-invasive and label-free detection of oral squamous cell carcinoma using saliva surface-enhanced Raman spectroscopy and multivariate analysis" Feb. 28, 2016 (Year: 2016).*

(Continued)

*Primary Examiner* — Maurice C Smith
(74) *Attorney, Agent, or Firm* — Blank Rome LLP

(57) ABSTRACT

The capabilities of using gold nanoparticle as surface-enhanced Raman scattering (SERS) substrate to obtain cervical smear harvested cells biochemical information for non-invasive cervical precancerous detection were presented in this patent document. A SERS reagent and a platform has been developed and optimized for the generation of a differential spectral fingerprinting for cervical cancer detection. SERS measurements were performed on three group's cervical exfoliated cell samples: one group from patients (n=36) with pathologically confirmed cervical cancer and another group with high-grade squamous intra- (Continued)

Figure 1:
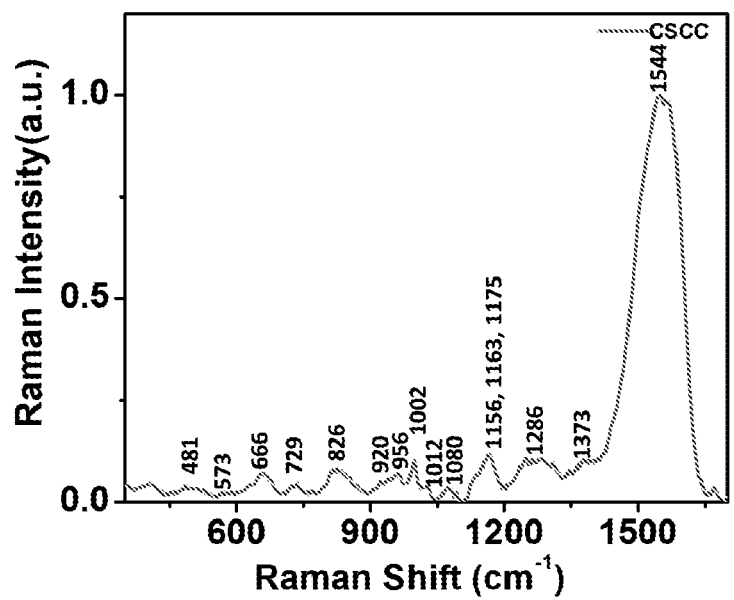

epithelial lesion (HSIL) (n=41) and the last group from healthy volunteers (control subjects, n=47). Tentative assignments of the Raman bands in the measured SERS spectra suggested interesting cancer specific biomolecular changes, including an increase in the relative amounts of amino acids, nucleic acid, carotenoid contents in the cell samples of cervical cancer patients as compared to that of healthy subjects. The results from this study demonstrated that gold nanoparticle based SERS substrate harvested exfoliated cervical smear cell analysis has tremendous potential for the non-invasive detection of cervical precancerous lesions.

7 Claims, 7 Drawing Sheets

(51) Int. Cl.
G01N 1/40 (2006.01)
G01N 1/28 (2006.01)
B82Y 40/00 (2011.01)

(52) U.S. Cl.
CPC ............ *G01N 21/658* (2013.01); *B82Y 40/00* (2013.01); *G01N 2001/4083* (2013.01)

(56) References Cited

U.S. PATENT DOCUMENTS

| | | | |
|---|---|---|---|
| 2007/0259437 A1* | 11/2007 | Natan | G01N 21/658 436/79 |
| 2010/0105053 A1 | 4/2010 | Cho et al. | |
| 2012/0257199 A1* | 10/2012 | Liu | G01N 21/658 356/301 |
| 2012/0328645 A1* | 12/2012 | Hoffman | A61K 39/015 424/191.1 |

OTHER PUBLICATIONS

Mariam M. Mirambo, "The use of 0.01M phosphate buffered saline as detection buffer for Alere Determine® HIV rapid test in resource limited settings", Apr. 2, 2017 (Year: 2017).*
S. Feng, et al., "Blood Plasma Surface-Enhanced Raman Spectroscopy for Non-Invasive Optical Detection of Cervical Cancer", Analyst, RSC Publishing, vol. 138, 2013, 3967-3974.
P. Kearney, et al., "Raman Spectral Signatures of Cervical Exfoliated Cells from Liquid-Based Cytology Samples", Journal of Biomedical Optics, BiomedicalOptics.SPIEDigitalLibrary.org, vol. 22, No. 10, 11 pgs., 2017.
S.A. Sanchez-Rojo, et al., "Cervical Cancer Detection Based on Serum Sample Surface Enhanced Raman Spectroscopy", Revista Mexicana de Fisica, vol. 62, 2016, pp. 213-218.
International Search Report & Written Opinion for PCT/IN2019/050540, dated Nov. 20, 2019, 10 pgs.

* cited by examiner

SCREENING KIT FOR DETECTION OF GRADES OF CERVICAL CANCER AND PROCESS FOR THE PREPARATION THEREOF

RELATED APPLICATIONS

This application is a national phase application of International Application No. PCT/IN2019/050540, filed on Jul. 24, 2019, which claims the benefit of Indian Patent Application No, 201811028087, filed on Jul. 26, 2018. The entire contents of these applications are hereby incorporated by reference.

FIELD OF INVENTION

The present invention relates to a screening kit for detection of different grades of cervical cancer. More, particularly the present invention relates to efficient platform developed to identify pre-cancerous lesions of the cervix viz.: (high-grade squamous intraepithelial lesion (HSIL) and cervical squamous cell carcinoma (CSCC) in the cells exfoliated from uterine cervix using a differential Raman spectral pattern.

BACKGROUND OF THE INVENTION

Cancer of the uterine cervix is one of the most common cancers among women worldwide and the second most prevalent cancers among women in India. It is considered as a preventable cancer as cervix is an easily amenable organ and occurrence of a heterogeneous spectrum of epithelial abnormalities (precancerous lesions) 10-15 years prior to the occurrence of invasive cancer has been well established (Sujathan et. al). The significance of Pap smear test for the detection and eradication of these precancerous lesions of cervix has been well documented. Based on this, systematically organized screening programmes for cervical cancer have been implemented in many of the developed countries. A rapid reduction in the incidence of this disease has been observed in countries like Sweden, Demark, Finland etc, where women have been covered by organized Pap smear screening programmes. The role of persistent infection with high risk HPV in cervical carcinogenesis is now well established and prophylactic vaccine against two of the high risk HPVs are currently available. Considering the several other high risk strains of this virus prevalent among the women, vaccine plus Pap smear test and HPV DNA test is now advocated for the effective control this disease. However, in India and many other low resource countries none of these measures have been implemented so far and cervical cancer continues to take extraordinary toll on the lives of our women. India contributes one fifth of the global burden of cervical cancer. As per the Globocan report of cervical cancer, around 528,000 estimated new cases with 266,000 death cases have been reported in 2012. Almost 9 out of 10 cervical cancer deaths occur in low resource countries including India. If we could also introduce population screening programmes, we could have saved the lives of our women. The major impediment for implementing screening programme by Pap smear is the lack of trained cytologists for microscopic analysis of the Pap smears of the eligible women of the community. So there is an urgent need for alternative cost effective and reliable method of screening without the requirement of highly trained cytologists.

Pap smear test is the microscopical analysis of cells which are naturally exfoliating from the squamocolumnar junction of cervix. These cells often stick to the cervical mucus which is collected by scraping with a spatula. These cells are studied for various morphological features of precancerous lesions (LSIL, HSIL etc) or malignancy. Since the precancerous lesions are asymptomatic, only through regular screening programmes it can be picked up. The microscopic analysis of cells require highly trained cytotechnologists. The doctor at the time of examination, visualize the cervix and collect a cell sample from the cervix and preserve in a preservative fluid. These cells are smeared onto a glass slide, stained with Pap stain and studied under microscope by trained cytotechnologists for morphological features and reported as normal or positive for precancerous lesions LSIL/HSIL or positive for malignancy. All positive samples are further confirmed by a cytopathologist. The smears are often reported as per the modified Bethesda system. The precancerous lesions are treated and followed up in a systematic way to ensure that the lesion is not progressing. As per the reports of the developed countries, where there is regular systematic screening program using Pap smear, more than 85% of the smears are within normal limits. So, if these normal smears can be screened out by a cost effective method, without utilizing the skilled cytotechnologists, the other 15% can be subjected to manual methods without over use of the resources.

Because skilled cytotechnologists are less available and as it is a tune consuming technique, some other alternative techniques are in high demand. The demand for specific and accurate cervical cancer screening has driven the development of novel diagnostic probes having high selectivity and sensitivity. Raman spectroscopy (RS) based on the inelastic light scattering can provide important biochemical information of macromolecules such as proteins, nucleic acids and lipids, because each molecule has its own pattern of vibrations that can serve as a Raman signature. Raman spectroscopy recently has emerged as a novel non-invasive diagnostic tool for cancer detection and identification of malignancy at different stages of neoplasia in tissues. Some groups have investigated the applications of Raman spectroscopy in differentiating normal and malignant tissues in various body sites, such as lungs, stomach, bladder, breast, parathyroid, prostate and cervix.

However, Raman scattering suffers the disadvantage of extremely poor efficiency due to its inherently small cross-section. Besides, the Raman spectra of biological samples are often superimposed on top of a strong fluorescence background that may be huge and make it difficult to extract the Raman signals. So in medical diagnosis these disadvantages make it a great challenge for practical applications of conventional Raman spectroscopy. There has been a great interest in Raman spectroscopy technique in the past two decades owing to the discovery of the surface-enhanced Raman scattering (SERS). Surface-enhanced Raman scattering was first reported by Fleischman et al. in 1974. Recent studies show have shown that with SERS technique, Raman signals can be enhanced by 10 to 14 orders of magnitude when the Raman active molecules are attached to nano-textured metallic surfaces, simultaneously with reduced autofluorescence background. SERS technology greatly improves the detection sensitivity of Raman spectroscopy, and has drawn considerable attention due to its great potential in biomedicine. SERS based immunoassay, which relies on a specific interaction between an antigen and a complementary antibody, is the strategy developed for most current oncology applications. Label-free SERS produces huge and complex data sets and it necessitates more refined analytical processes to mine substantial information from the spectral data. A great inconsistency in the intensity and spatial scattering generated due to the variable deposition and orientation of gold nanoparticles reduces the clarity of spectral data obtained. Even though such challenges are existing, introduction of chemometric analysis like Principal Component Analysis (PCA), Linear Discriminant Analysis (LDA), Cluster Analysis, Support Vector Machine Analysis (SVM) have enriched or improved the spectral data sets for classification and characterization.

For cervical cancer, smears made from scraped cervical exfoliated cells is the accepted screening method which can be taken conveniently and even continuously throughout the treatment for diagnosed patient without causing pain in a non-invasive manner and biopsy is done for confirmation of high grade lesions and invasive carcinoma. All studies reported earlier used tissue samples for Raman measurements rather than cell samples. Collection of tissue sample needs surgical procedures and hence cannot be suggested for screening purpose. Gold nanoparticles (AuNPs) are used in this study as SERS substrate because of their favorable physical, chemical properties and biocompatibility.

In this invention, we explored the use of AuNPs for SERS spectral evaluation in cervical exfoliated cells in order to find out the biochemical changes which could able to differentiate between NRML, HSIL and CSCC patients by distinct changes in Raman fingerprints of variable abundance of intracellular amino acids with associated proteins, lipids, nucleic acids, DNAs and variables viz., amide II, amide III etc. To our knowledge, this is the first report on SERS based analysis of cervical exfoliated cells using a label free nanoformulation with AuNPs for cervical precancerous detection. The results showed significant level of differentiation between three classes using single cell, cell pellet and extracted DNA measurements.

Definitions

Figure 2:
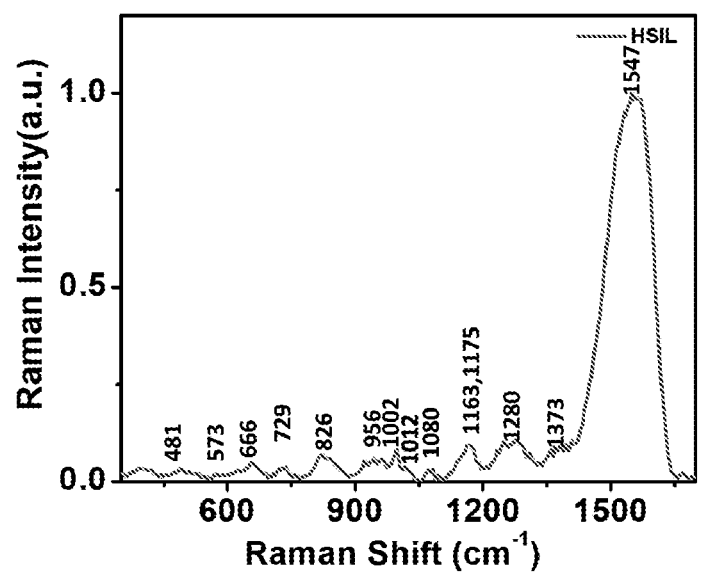
Figure 3:
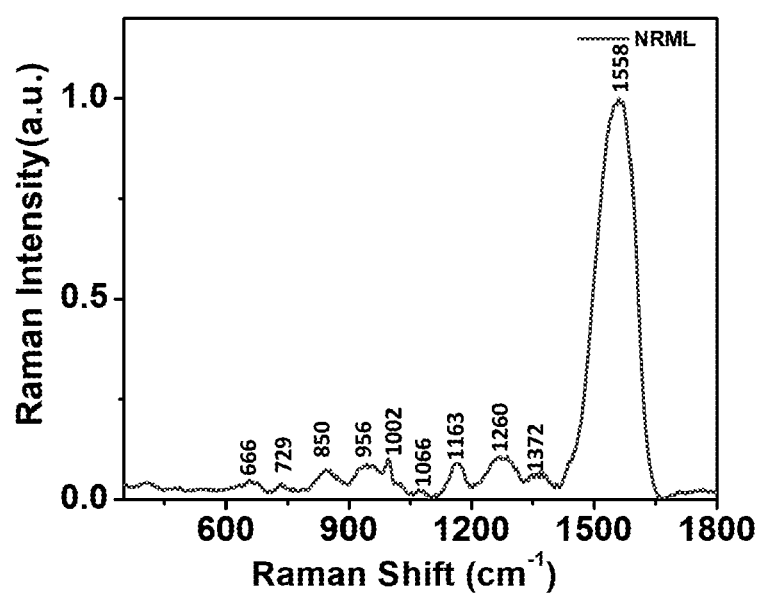
Figure 4:
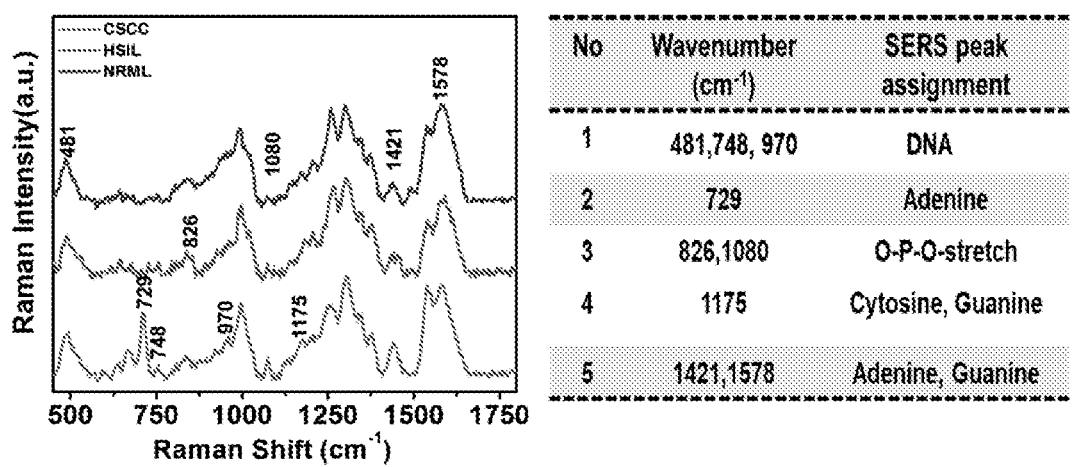
Figure 5:
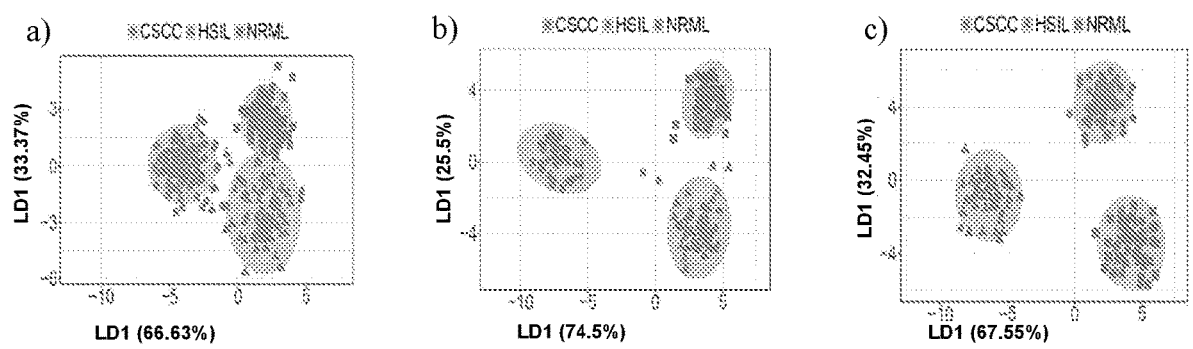
Figure 6:
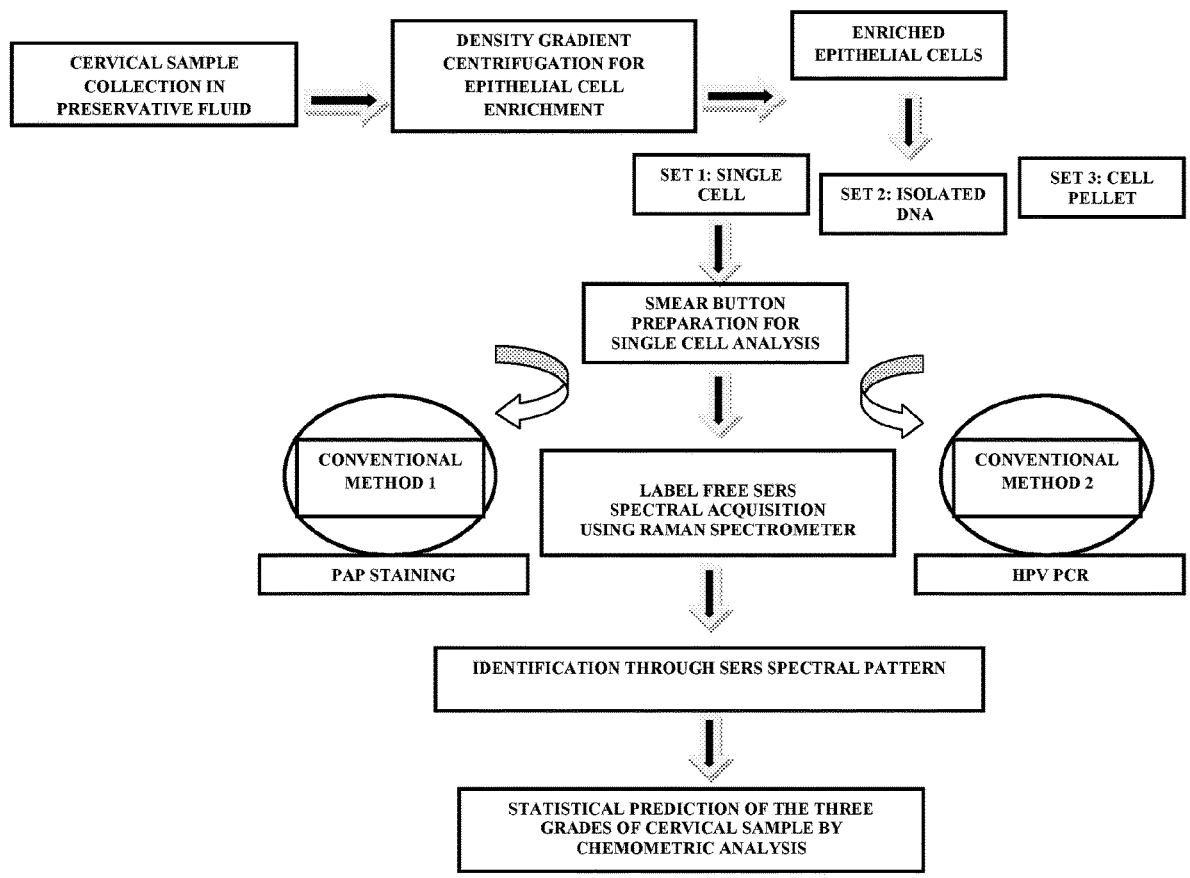
Figure 7:
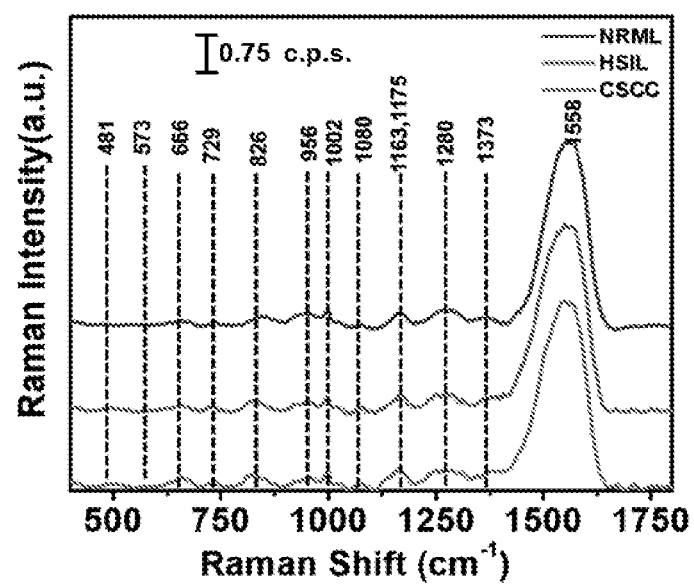

AuNPs—Gold nano-particles
NRML—Normal
HSIL—high-grade squamous intraepithelial lesion
CSCC—cervical squamous cell carcinoma (iv) BRIEF DESCRIPTION OF THE DRAWINGS The objects and features of the present invention will become apparent from the following description of the invention, when taken in conjunction with the accompanying drawings, which respectively show FIG. 1: Representative spectrum for CSCC sample from 400 $cm^{-1}$ to 1800 $cm^{-1}$ FIG. 2: Representative spectrum for HSIL sample from 400 $cm^{-1}$ to 1800 $cm^{-1}$ FIG. 3: Representative spectrum for NRML sample from 400 $cm^{-1}$ to 1800 $cm^{-1}$ FIG. 4: Differential spectra for DNA samples from NRML, HSIL and CSCC (500 $cm^{-1}$ to 1800 $cm^{-1}$) and its respective peak assignments FIG. 5: Linear discriminant analysis in a) Single cell, b) Cell pellet, c) Extracted DNA FIG. 6: Scheme representing the overall work FIG. 7: Comparison of mean SERS spectral peak from NRML, HSIL and CSCC samples.

OBJECTIVES OF THE INVENTION

The main objective of the invention relates to a kit for screening of different grades of cervical cancer Another objective of the present invention is to provide the abundance of the three grades viz. NRML, HSIL, and CSCC by Raman fingerprint analysis.

Yet another objective of the present invention is to provide the validation of the signature spectra viz., presence of amino acids associated proteins, lipids, nucleic acids, DNAs, in terms of peak intensity, peak shift with sufficient number of patient samples.

Still another objective of the present invention is differential recognition, sensitivity, specificity, and prediction accuracy to be validated by chemometric analysis.

SUMMARY OF THE INVENTION

Accordingly, the present invention provides a label free detection kit useful in SERS based platform for three major grades of exfoliated cells obtained from cervix with simple processing and utilization of specified concentration of AuNPs as SERS substrate winch designated by significant Raman spectral pattern of biomolecular fingerprint between healthy subjects, high-grade squamous intraepithelial lesion (HSIL) and cervical squamous cell carcinoma (CSCC) patients Raman intensity difference together with specific peak assignments measured SERS bands make it clear that benign and malignant cervical tumors gave rise to the structural and specific biomolecular changes of cervical epithelial cells, including the relative amounts of various biomolecules like DNA, protein, lipids etc. Carotenoid peak with significant intensity is high in the case of cancer samples. These variations may be connected to metabolic changes among normal to carcinoma samples. These results from this exploratory study demonstrated the great potential of cervical cancer by SERS based platform as a clinical tool for label-free, noninvasive, and convenient for the diagnosis of early stages of cancer detection and screening.

In an embodiment of the present invention it provides a kit for screening of different grades of cervical cancer comprising of:
a) Gold (AuNP) Nanoparticle having size in the range of 40-50 nm nm as the SERS substrate.
b) Preservative fluid comprising of >50% Ethanol, Methanol, Isopropanol, Formaldehyde, Saline solution, Di-potassium hydrogen phosphate.
c) Density gradient solution comprising of 20-50% (w/v) of sucrose in MilliQ water
d) Phosphate Buffered Saline (PBS) composed of Sodium Chloride, Potassium Chloride, Disodium phosphate, Potassium dihydrogen phosphate.
e) Pre-coated glass slide comprising of Poly-L-lysine, APES [(3-Aminopropyl) triethoxy silane, for the effective attachment of sample. (Surface enhanced Raman scattering PLATFORM).

In an embodiment of the present invention it provides a kit where in the concentration of the nanoparticle is in the range of $8-10 \times 10^{13}$ particles/ml.

In an embodiment of the present invention it provides a kit where in the preservative fluid used for fixing the sample on the slide is selected from the group comprising of >50% Ethanol, Methanol, Isopropanol, Formaldehyde, Saline solution, Di-potassium hydrogen phosphate.

In an embodiment of the present invention it provides a kit where in the density gradient solution comprises of 20-50% (w/v) of sucrose in MilliQ water.

In an embodiment of the present invention it provides a kit where in the Phosphate buffered saline comprises of Sodium Chloride, Potassium Chloride, Disodium phosphate, Potassium dihydrogen phosphate.

In an embodiment of the present invention it provides a kit where in the glass slide is coated with compound selected from the group comprising of PolyL-lysine, APES [(3-Aminopropyl) triethoxy silane for adhesion of cells in the glass slide.

In yet another embodiment of the present invention it provides a kit where in the different grades of cervical cancer is selected from the group consisting of NRML (Normal), HSIL (High-grade Squamous Intraepithelial Lesion), CSCC (Cervical Squamous Cell Carcinoma).

In yet another embodiment of the present invention it provides a method for detection of different stages of cervical cancer comprising the following steps:
  a. Providing cell samples in preservative fluid comprising of >50% Ethanol, Methanol, Isopropanol, Formaldehyde, Saline solution, Di-potassium hydrogen phosphate.
  b. Centrifuging the cell samples obtained in step a to obtain a pellet by using density gradient fluid comprising of 20-50% (w/v) of sucrose in MilliQ water to enrich the more denser epithelial cells as a pellet in the bottom of the tube and less denser interfering cells like RBCs, polymorphs, inflammatory cells, mucus will be cleared in the supernatant.
  c. Resuspending the cell pellet obtained in step b in PBS buffer comprising of Sodium Chloride, Potassium Chloride, Disodium phosphate, Potassium dihydrogen phosphate.
  d. Providing glass slide pre-coated with compounds comprising of Poly-L-lysine, APES [(3-Aminopropyl) triethoxy silane.
  e. Dropping down the suspension obtained in step C onto pre-coated glass slide obtained in step d;
  f. Incubation of dropping down cell suspension onto pre-coated glass slide obtained in step e with AuNPs approximately 10-30 minutes.
  g. Measuring the surface enhanced Raman scattering from the cell samples and analyzed the Raman spectral pattern to differentiate the three grades i.e. NRML, HSIL and CSCC.

DETAILED DESCRIPTION OF THE INVENTION

A SERS based diagnostic platform extended with a kit including gold nanoparticles, AuNPs (40-50 nm) 8 to $10 \times 10^{13}$ particles/ml as the SERS substrate for differentiation of NRML, HSIL and CSCC of the cervical exfoliated cells. Our ultimate aim is to validate the differential spectral pattern utilizing the SERS-nanoformulation which distinctly recognizes the HSIL and CSCC cells from NRML within the exfoliated cells collected from the cervix. This study was approved by the local Ethics Committee. Prior to specimen collection, all patients have signed informed consent forms. Pathologically confirmed cervical smears, NRML, HSIL and CSCC are collected in BD preservative fluid using speculum. Density gradient centrifugation was performed to bring down the epithelial cells as a pellet. The pellet was then re-suspended in PBS buffer and dropped as a smear button in a glass slide. SERS spectral analysis was done using 9:1 ratio of AuNPs and sample (8 to $10 \times 10^{13}$ particles/ml) with diode laser of 633 nm laser excitation source with spectrograph grating 600 gr/mm using maximum 10-20 sec integration time and around 10-15 accumulations. Single cells, cell pellet and extracted DNA was investigated in order to differentiate the three categories. NRML has comparatively less intense peaks than HSIL and CSCC samples when normalized to its highest peaks. The significant SERS spectral signatures between NRML, HSIL and CSCC were observed to be 481, 573, 666, 729, 826, 956, 1002, 1080, 1163, 1175, 1286, 1373 and 1558 $cm^{-1}$. Overall aromatic amino acid peaks like tryptophan, tyrosine and phenyl alanine were prominent in the SERS spectrum showed an incremental increase in intensity from HSIL and CSCC when compared to NRML. A prominent peak at 1080 $cm^{-1}$ corresponding to phosphate backbone of nucleic acids were evident in CSCC samples with a shift in NRML sample at 1066 $cm^{-1}$. Amide III signal was found to be higher in HSIL and CSCC while Amide II showed a shift between the NRML, HSIL and CSCC samples. Linear discriminant analysis showed a 14 nm shift between the NRML and CSCC samples, 11 nm shift between NRML and HSIL samples, 3 nm shift between HSIL and CSCC samples. Linear discriminant analysis showed a clear discrimination between NRML, HSIL and CSCC samples in whole cells, cell pellet and extracted DNA. In addition, chemometric analysis through Support Vector Machine (SVM) analysis showed a prediction accuracy of >90% with a standard deviation of <1% for single cell, >75% predication accuracy with a standard deviation of <1% for cell pellet and >90% prediction accuracy with a standard deviation of <4% for extracted DNA.

EXAMPLES

The following examples are given by way of illustration of the present invention and therefore should not be construed to limit the scope of the present invention.

Example-1

Preparation of SERS Based Screening Kit:
  (i) Synthesis and Optimization of the concentration of Gold Nanoparticle (AuNPs) for label free detection.
    Gold nanoparticles (AuNPs, size around 40-50 nm) was prepared by well-established citrate reduction method. The characterization of the synthesized nanoparticles were performed through UV-vis spectroscopy, Dynamic Light Scattering (DLS) and High Resolution Transmission Electron Microscopy (HR-TEM). The size was approximately 40-50 nm which serves as an optimal performing SERS substrate.
  (ii) Optimum concentration of AuNPs which will provide maximum Raman signal intensity; Optimum concentration has been evaluated (AuNPs 8 to $10 \times 10^{13}$ particles/ml) which provided the maximum SERS intensity.
  (iii) A preservative fluid was prepared for preservation and fixation of the sample collected comprising of >50% Ethanol, Methanol, Isopropanol, Formaldehyde, Saline solution, Di-potassium hydrogen phosphate.
  (iv) A density gradient solution was prepared comprises of 20-50% (w/v) of sucrose in MilliQ water for enriching the epithelial cells in the samples.
  (v) A phosphate buffered saline buffer was prepared comprises of Sodium Chloride, Potassium Chloride, Disodium phosphate, Potassium dihydrogen phosphate for resuspension of cell pellet.
  (vi) SERS platform consist of glass slide coated with comprising of PolyL-lysine, APES [(3-Aminopropyl) triethoxy silane] for adhesion of cells sample in the glass slide.

Example-2

SERS Fingerprint from Exfoliated Cells

The exfoliated cell samples were collected in the preservative solution comprising of >50% Ethanol, Methanol, Isopropanol, Formaldehyde, Saline solution, Di-potassium hydrogen phosphate. Density gradient centrifugation was performed using sucrose as gradient solution to enrich the epithelial cells in the cervical smear samples. The pellet obtained was resuspended in the PBS buffer comprising Sodium Chloride, Potassium Chloride, Disodium phosphate, Potassium dihydrogen phosphate. The resuspended solution was dropped in the glass slide coated with Poly L-lysine, APES [(3-Aminopropyl) triethoxy silane. After 10-30 minutes incubation, the excess fluid is discarded and the slide is stored in absolute ethanol till SERS measurement. Single cell has been focused bright field and spectra have been taken from different fields of the cell. A number of spectra have been taken from random locations of the cells and also from nucleus after morphologically suspected normal and abnormal cell identification. The ratio of nuclear size to cytoplasm has been taken as a feature for morphological discrimination parameter for taking the SERS measurements. SERS spectral analysis is done using AuNPs with a concentration of 8 to $10 \times 10^{13}$ particles/ml) and analyzed through diode laser of 633 nm laser excitation source with spectrograph grating 600 gr/mm setting 10-15 sec integration time and 10-20 accumulations. The laser power is between 3-7 mW. The fingerprint region 400 $cm^{-1}$ to 1800 $cm^{-1}$ was analyzed for the spectral differences between the three classes.

- Signature Raman spectra obtained due to the abundance of amino acids associated proteins, lipids, nucleic acids, DNAs, in terms of peak intensity, peak shift with a sufficient number of patient samples
- Differential recognition: Specificity, specificity and prediction accuracy obtained by chemometric analysis.

Example-3

Single Cell Spectral Analysis from Cervical Squamous Cell Carcinoma (CSCC)

The CSCC samples were collected in the preservative solution comprising of >50% Ethanol, Methanol, Isopropanol, Formaldehyde, Saline solution, Di-potassium hydrogen phosphate. Density gradient centrifugation was performed using sucrose as gradient solution to enrich the epithelial cells in the cervical smear samples. The pellet obtained was resuspended in the PBS buffer comprising Sodium Chloride, Potassium Chloride, Disodium phosphate, Potassium dihydrogen phosphate. The resuspended solution was dropped in the glass slide coated with PolyL-lysine, APES [(3-Aminopropyl) triethoxy silane. After 10-30 minutes of incubation, the excess fluid is discarded and the slide is stored in absolute ethanol till SERS measurement.

CSCC cells are having a variety of peaks in the range 400-1800 $cm^{-1}$ including 481, 573, 666, 729, 826, 920, 956, 1002, 1012, 1080, 1156, 1163, 1175, 1286, 1373, 1544 $cm^{-1}$ The aromatic amino acids, tryptophan, tyrosine and phenyl alanine peak has significant intensity in CSCC samples. Tryptophan abundance were evident from the peak at 573 $cm^{-1}$ peak. Tyrosine peaks at 1163 $cm^{-1}$ were prominent in CSCC samples. Phenyl alanine peak at 1002 $cm^{-1}$ in all samples showed a shoulder peak at 1012 $cm^{-1}$ in HSIL and CSCC samples. Carotenoid peak at 956 and 1156 $cm^{-1}$ is having significant intensity which helps the cancer cells to resist damage and also helps the cancer cells in the synthesis of large amount of glycoproteins. The PO2 stretching of nucleic acid at 1066 $cm^{-1}$ in NRML samples have a significant increase and shift to 1080 $cm^{-1}$ respectively in HSIL and CSCC sample. The $PO_2$ stretching peak at 826 $cm^{-1}$ which shows DNA content increase is prominent in HSIL and CSCC samples which is absent in NRML. The nucleic acid bases cytosine, guanine, adenine and thymine peaks at 666, 729, 1175, 1373 $cm^{-1}$ were prominent in the CSCC samples. The Amide III signal were shifted to 1286 $cm^{-1}$ in CSCC samples from 1260 $cm^{-1}$ in NRML samples and found to be prominent in CSCC while Amide II showed a shift from 1558 $cm^{-1}$ in NRML to 1544 $cm^{-1}$ in CSCC samples. Linear discriminant analysis showed a clear discrimination of carcinoma sample from NRML, HSIL and CSCC samples in single cell, cell pellet and extracted DNA.

Example-4

Single Cell Spectral Analysis from High-Grade Squamous Intraepithelial Lesion (HSIL)

The HSIL samples were collected in the preservative solution comprising of >50% Ethanol, Methanol, Isopropanol, Formaldehyde, Saline solution, Di-potassium hydrogen phosphate. Density gradient centrifugation was performed using sucrose gradient solution to enrich the epithelial cells in the cervical smear samples. The pellet obtained was resuspended in the PBS buffer comprising Sodium Chloride, Potassium Chloride, Disodium phosphate, Potassium dihydrogen phosphate. The resuspended solution was dropped in the glass slide coated with either PolyL-lysine, APES [(3-Aminopropyl) triethoxy silane. After 10-30 minutes of incubation, the excess fluid is discarded and the slide is stored in absolute ethanol till SERS measurement.

Cells from HSIL were found to have significant signature peaks in the range 400-1800 $cm^{-1}$ including 481, 573, 666, 729, 826, 956, 1002, 1012, 1080, 1163, 1175, 1280, 1373 and 1547 $cm^{-1}$. Peaks at 1012 $cm^{-1}$ and 573 $cm^{-1}$ showed the increasing activity of abnormality in HSIL samples which is assigned to phenyl alanine and tryptophan respectively. The nucleic acid peak at 826 $cm^{-1}$ have been shifted in HSIL and CSCC samples. A peak at 1080 $cm^{-1}$ assigned to PO2 stretching has been slightly increased which shows the increasing abundance of nucleic acids, but is lesser than CSCC samples. A peak at 1175 $cm^{-1}$ showed the increase of cytosine, guanine in HSIL samples. 1280 $cm^{-1}$ peak was assigned to Amide III which is also shifted when compared with NRML and CSCC. 1547 $cm^{-1}$ peak was assigned to Amide II which is also slightly shifted from 1544 $cm^{-1}$ in CSCC samples.

Example-5

Single Cell Spectral Analysis from Normal (NRML)

The NRML samples were collected in the preservative solution comprising of >50% Ethanol, Methanol, Isopropanol, Formaldehyde, Saline solution, Di-potassium hydrogen phosphate. Density gradient centrifugation was performed using sucrose gradient solution to enrich the epithelial cells in the cervical smear samples. The pellet obtained was resuspended in the PBS buffer comprising Sodium Chloride, Potassium Chloride, Disodium phosphate, Potassium dihydrogen phosphate. The resuspended solution was dropped in the glass slide coated with either PolyL-lysine, APES [(3-Aminopropyl) triethoxy silane. After 10-30 minutes of incubation, the excess fluid is discarded and the slide is stored in absolute ethanol till SERS measurement.

Normal cells showed signature peaks in the range 400-1800 cm$^{-1}$ including 666, 729, 850, 956, 1002, 1066, 1163, 1260, 1373 and 1558 cm$^{-1}$. Peaks at 1002 cm$^{-1}$ showed the presence of phenyl alanine. A slight peak at 1066 cm$^{-1}$ was found associated with nucleic acid PO$_2$ stretching which is shifted to 1080 cm$^{-1}$ prominently in CSCC samples. The 1163 cm$^{-1}$ peak was associated with lipids C=C stretch and tyrosine. The amide III peak at 1260 cm$^{-1}$ was prominent in normal samples. The amide II peak showed at 1558 cm$^{-1}$ which was significantly shifted in HSIL and CSCC samples.

Example-6

Differences Between the CSCC, HSIL and NRML Exfoliated Cervical Cells and the SERS spectral analysis using AuNPs were carried out. A number of spectra have been taken with a specified proportion of AuNPs with laser of 633/786 nm laser excitation source with spectrograph grating 600 gr/mm/1200 gr/mm having 10-15 sec integration time and 10-20 accumulations. The laser power has been used in between 3-7 mW. The fingerprint region 400 to 1800 cm$^{-1}$ was analyzed for the spectral differences between the three classes. 729, 1175 and 1421 and 1578 cm$^{-1}$ corresponding to nucleobases were prominent in abnormal DNA samples. The phosphate backbone of nucleic acid is evident significantly at 826 and 1080 cm$^{-1}$ peaks.

Example-9

Chemometric Analysis

Validation of spectral differences between NMRL, HSIL and CSCC through statistical analysis. All statistical analysis

| NRML | HSIL | CSCC |
|---|---|---|
| Major signature peaks 666, 729, 850, 956, 1002, 1066, 1163, 1260, 1373 and 1558 cm$^{-1}$ | Major signature peaks 481, 573, 666, 729, 826, 956, 1002, 1012, 1080, 1163, 1175, 1280, 1373 and 1547 cm$^{-1}$ | Major signature peaks 481, 573, 666, 729, 826, 920, 956, 1002, 1012, 1080, 1156, 1163, 1175, 1286, 1373, 1544 cm$^{-1}$ |
| Nucleic acid PO$_2$ stretching at 826 cm$^{-1}$ is shifted to 850 | 826 cm$^{-1}$ is prominent in | 826 cm$^{-1}$ is significantly increased. |
| The nucleobases at 666, 729, 1175, 1373 and 1421 cm−1 are not prominent | The nucleobases at 666, 729, 1175 and 1373 is prominent than normal samples | The nucleobases at 666, 729, 1175 and 1373 cm$^{-1}$ is prominent |
| Tryptophan peak at 573 cm$^{-1}$ is not prominent. | Tryptophan peak prominent than normal samples | Tryptophan peak at 573 cm$^{-1}$ is prominent |
| Phenyl alanine peak at 1002 cm$^{-1}$ | Phenyl alanine peak shifted to 1012 cm$^{-1}$ | Phenyl alanine peak shifted to at 1012 cm$^{-1}$ |
| Tyrosine not prominent | Tyrosine not prominent | Tyrosine peak at 1163 cm$^{-1}$ is prominent |
| No prominent peak | Slight peak corresponding to 956 cm$^{-1}$ carotenoid is present | A carotenoid peak at 956 and 1156 cm$^{-1}$ is prominent |
| Nucleic acid PO$_2$ stretching at 1066 cm$^{-1}$ | PO$_2$ stretching shifted to 1080 cm$^{-1}$ | PO$_2$ stretching at 1080 cm$^{-1}$ is prominent |
| Amide III peak at 1260 cm$^{-1}$ | Amide III peak shifted to 1280 cm$^{-1}$ | Amide III peak shifted to 1286 cm$^{-1}$ |
| Amide II peak at 1558 cm$^{-1}$ | Amide II peak shifted to 1547 cm$^{-1}$ | Amide II peak shifted to 1544 cm$^{-1}$ |

Example-7

Cell Pellet Spectral Analysis

The exfoliated cell samples were collected in the preservative solution comprising of >50% Ethanol, Methanol, Isopropanol, Formaldehyde, Saline solution, Di-potassium hydrogen phosphate. Density gradient centrifugation was performed using sucrose gradient solution to enrich the epithelial cells in the cervical smear samples. The cell pellet obtained was resuspended in the PBS buffer comprising Sodium Chloride, Potassium Chloride, Disodium phosphate, Potassium dihydrogen phosphate.

The cell pellet is directly mixed with AuNPs and SERS spectral analysis was carried out. Because of the heterogeneous nature of the pellet which comprises of both normal and abnormal cells, a mixture of signature Raman spectra were acquired and nearly 75% prediction accuracy was obtained through SVM analysis.

Example-8

DNA Spectral Analysis

DNA was isolated from different NRML, HSIL and CSCC samples collected in the preservative solution comprising of >50% Ethanol, Methanol, Isopropanol, Formaldehyde, Saline solution, Di-potassium hydrogen phosphate including PCA, LDA and SVM analysis were done using R software. Intra group variations can occur due to noise during acquisition of Raman data from cells which lead to reduction of specificity of the PCA. Hence we further adopted LDA and SVM for further analysis.

Linear Discriminant Analysis (LDA)

For classification, LDA is better by theory and concept. LDA is used for analyzing variables in studied groups which are statistically significant. Clear demarcation between all the three samples was obtained for NRML, HSIL and CSCC.

Support Vector Machine (SVM)

Support Vector Machine are supervised learning models or a machine learning technique with algorithms that analyse data for classification and regression analysis. Analysis were done by randomly selecting 75% of the spectra as the train set and rest 25% were used as the test set. The SVM analysis were repeated with 500 different random samples and measured the average prediction accuracy. The accuracy were found above 90% for single cell, 75% for cell pellet and 90% for extracted DNA respectively.

|       | NRML | HSIL   | SCC |
|-------|------|--------|-----|
| CELL  |      |        |     |
| NRML  | 9    | 0      | 322 |
| HSIL  | 17   | 49     | 3   |
| SCC   | 226  | 4      | 2   |
| Prediction accuracy |  | 93.84% |  |
| Standard deviation  |  | 0.73%  |  |
| PELLET |     |        |     |
| NRML  | 5    | 0      | 31  |
| HSIL  | 6    | 3      | 7   |
| SCC   | 24   | 0      | 5   |
| Prediction accuracy |  | 74.26% |  |
| Standard deviation  |  | 0.05%  |  |
| DNA   |      |        |     |
| NRML  | 19   | 0      | 0   |
| HSIL  | 0    | 13     | 0   |
| SCC   | 1    | 0      | 11  |
| Prediction accuracy |  | 92.21% |  |
| Standard deviation  |  | 3.84%  |  |

Support Vector Machine analysis in a) Single cell, b) Cell pellet, c) Extracted DNA

ADVANTAGES OF THE INVENTION

The main advantages of the present invention are as follows.
1. It provides a significant difference of SERS spectral pattern of NRML, HSIL and CSCC were found through SERS based label free detection.
2. As immunostaining is a time consuming and skilled cytotechnologists are required for correct evaluation and HPV, PCR causes nonspecific amplification of abnormal samples irrespective of its grades and expensive, SERS is an accurate, simple and reliable technique which can differentiate normal, HSIL and cancerous samples through its differential spectra.
3. It provides a diagnostic screening kit which differentiated the grades of cervical cancer exfoliated cells through a label free detection platform using surface enhanced Raman scattering (SERS) technique.
4. The screening kit adopted a new SERS technique which enriched the cervical exfoliated cells in order to get maximum differentiation of three grades.
5. It provides the abundance of aromatic amino acids like tryptophan, phenyl alanine and tyrosine and their specific peak shifts which differentiated significantly between NRML, HSIL and CSCC.
6. It provides the nucleic acid bases i.e. cytosine, guanine, adenine peaks at 666, 729, 1175, 1373 $cm^{-1}$ prominent in the CSCC samples.
7. It provides the major identification of carotenoid peak at 956 and 1.1.56 $cm^{-1}$ with high intensity got in CSCC samples which were not prominent in normal samples.
8. The identification of $PO_2$ stretching of nucleic acid which showed the increase in DNA seen at 1070-1090 $cm^{-1}$ range specific only to HSIL and CSCC positive samples.
9. It provides the Amide III peak and Amide II at 1260 and 1558 $cm^{-1}$ showed a prominent shift in HSIL and CSCC samples.
10. It provides the Raman spectra has been evaluated through chemometric analysis which showed more than 80% sensitivity in cell samples and can be utilized as reference spectra for screening of cervical precancerous lesions.

We claim:
1. A kit for screening different grades of cervical cancer comprising:
   a) Gold Nanoparticles (AuNPs) having size in a range of 40-50 nm as a Surface Enhanced Raman Scattering (SERS) substrate;
   b) a preservative fluid;
   c) a density gradient solution;
   d) a Phosphate Buffered Saline (PBS); and
   e) a pre-coated glass slide; wherein the density gradient solution is 20-50% (w/v) of sucrose in MilliQ water.
2. The kit as claimed in claim 1, wherein the gold nanoparticles are in a concentration in a range of $8\text{-}10 \times 10^{13}$ particles/ml.
3. The kit as claimed in claim 1, wherein the preservative fluid used for fixing a sample on the pre-coated glass slide is selected from a group consisting of >50% Ethanol, Methanol, Isopropanol, Formaldehyde, Saline solution, and Di-potassium hydrogen phosphate.
4. The kit as claimed in claim 1, wherein the phosphate buffered saline comprises Sodium Chloride, Potassium Chloride, Disodium phosphate, and Potassium dihydrogen phosphate.
5. The kit as claimed in claim 1, wherein the pre-coated glass slide is pre-coated with a compound selected from the group consisting of Poly-L-lysine, and APES [(3-Aminopropyl) triethoxy silane.
6. The kit as claimed in claim 1, wherein the different grades of cervical cancer is selected from the group consisting of NRML (Normal), HSIL (High-grade Squamous Intraepithelial Lesion), and CSCC (Cervical Squamous Cell Carcinoma).
7. A method for detection of different grades of cervical cancer consisting, of the following steps:
   a) Providing cell samples in a preservative fluid selected from the group consisting of >50% Ethanol, Methanol, Isopropanol, Formaldehyde, Saline solution, and Di-potassium hydrogen phosphate;
   b) Centrifuging the cell samples obtained in step a to obtain a cell pellet by using a density gradient fluid comprising 20-50% (w/v) of sucrose in MilliQ water;
   c) Resuspending the cell pellet obtained in step b in a PBS buffer comprising Sodium Chloride, Potassium Chloride, Disodium phosphate, and Potassium dihydrogen phosphate to obtain a cell suspension;
   d) Providing a glass slide pre-coated with compounds comprising Poly-L-lysine, and APES [(3-Aminopropyl) triethoxy;
   e) Dropping down the cell suspension obtained in step c onto the pre-coated glass slide obtained in step d;
   f) Incubating the dropped down cell suspension onto the pre-coated glass slide obtained in step e with cold nanoparticles (AuNPs) for 10-30 minutes; and
   g) Measuring surface enhanced Raman scattering (SERS) from the cell samples and analyzing Raman spectral pattern to differentiate three grades of cervical cancer selected from the group consisting of NRML, HSIL and CSCC.

* * * * *